United States Patent [19]

Saavedra et al.

[11] Patent Number: 5,814,656
[45] Date of Patent: Sep. 29, 1998

[54] SELECTIVE PREVENTION OF ORGAN INJURY IS SEPSIS AND SHOCK USING SELECTIVE RELEASE OF NITRIC OXIDE VULNERABLE ORGANS

[75] Inventors: Joseph E. Saavedra, Thurmont; Larry K. Keefer, Bethesda, both of Md.

[73] Assignee: The United States Of America, as represented by the Department Of Health And Human Services, Washington, D.C.

[21] Appl. No.: 942,896

[22] Filed: Oct. 2, 1997

Related U.S. Application Data

[62] Division of Ser. No. 509,558, Jul. 31, 1995, Pat. No. 5,714,511.

[51] Int. Cl.$^6$ .......................... A61K 31/40; A61K 31/535; A61K 31/495; A61K 31/445

[52] U.S. Cl. .................... 514/426; 514/237.8; 514/255; 514/315; 514/611; 546/244; 548/557; 564/81; 564/113; 544/164; 544/382

[58] Field of Search ................... 514/237.8, 255, 514/315, 611, 426; 544/164, 382; 546/244; 548/557; 564/81, 113

[56] References Cited

U.S. PATENT DOCUMENTS 5,366,997  11/1994  Keefer et al. ............................ 514/611

*Primary Examiner*—Raymond Henley, III
*Attorney, Agent, or Firm*—Leydig, Voit & Mayer, Ltd.

[57] ABSTRACT

A method for the treatment of mammalian tissue injured or at risk of injury during sepsis or shock including the administration to a mammal a diazeniumdiolate which releases a therapeutically effective amount of nitric oxide sufficient to protect the tissue from sepsis- or shock-induced injury.

9 Claims, 4 Drawing Sheets

SELECTIVE PREVENTION OF ORGAN INJURY IS SEPSIS AND SHOCK USING SELECTIVE RELEASE OF NITRIC OXIDE VULNERABLE ORGANS

This is a divisional of U.S. application No. 08/509,558 filed Jul. 31, 1995, now U.S. Pat. No. 5,714,511.

TECHNICAL FIELD OF THE INVENTION

The present invention relates to a method for the treatment of sepsis and of shock. More particularly, the present invention is directed to a method for the treatment of sepsis and shock using nitric oxide-containing compounds that selectively release nitric oxide under physiological conditions in vulnerable organs to prevent organ injury.

BACKGROUND OF THE INVENTION

Sepsis is generally understood to be the presence in the blood or tissues of various pus-forming and other pathogenic organisms or their toxins. Cecil, Textbook of Medicine 17th Ed., W. B. Saunders Company pp. 1473–1476, 1985. Serious complications arise when the infection spreads from the original site to the bloodstream. The presence of viable bacteria in the bloodstream can lead to both microbiologic complications and inflammatory complications. Microbiologic complications are known to cause direct tissue or organ damage. Inflammatory complications can result in tissue or organ damage independent of the toxins produced by the bacterium itself. The end stage of the various indications of sepsis is the systemic vascular collapse commonly known as septic shock.

Typically, treatment of sepsis has involved the use of antibiotics and anti-inflammatory agents. The therapy of shock associated with sepsis involves volume replacement as an essential component. Sufficient quantities of an appropriate solution, including, where appropriate, whole blood, are administered to the septic patient in an effort to provide the requisite volume support.

Within the last several years, it has been suggested that the release of NO might be involved in sepsis shock. Wright et al. "Protective and Pathological Roles of Nitric Oxide in Endotoxin Shock" Cardiovascular Research 26, pp. 48–57, 1992. Wright et al. conclude that the use of an inhibitor of both the $Ca^{2+}$ dependent and $Ca^{2+}$ independent nitric oxide synthesis in the treatment of lipopolysaccharide induced shock in anaesthetized New Zealand white rabbits was deleterious. The use of an NO donor such as S-nitroso-N-acetyl-penicillamine (SNAP) was suggested to overcome the deleterious effect of NO synthase inhibition. Interestingly, however, a Letter to the Editor by Meyer and Traber suggests that the study of Wright et al. was incomplete and that NO synthesis inhibition in a model of hyperdynamic sepsis completely reversed the alteration in hyperdynamic endotoxemia. Symington et al. "Protective Action of S-Nitroso-N-Acetylpenicillamine (SNAP) in a Rat Model of Hemorrhagic Shock" *Meth Find Exp. Clinical Pharmacol* 1992, 14(10):789–797 discuss the use of the NO donor SNAP in hemorrhagic shock and suggest that they have shown significant protective effects of SNAP in hemorrhagic shock in rats. Carey et al. "Antishock and Endothelial Protective Actions of a NO Donor in Mesenteric Ischemia and Reperfusion" *Circulatory Shock* 38:209–216 (1992) discusses the use of nitric oxide (NO) donors known as sydnonimines which are stated to spontaneously liberate NO at a physiological pH for circulatory shock. The authors conclude that the NO donor compound exhibited a protective effect in mesenteric ischemia reperfusion in cats.

The nitric oxide-releasing compounds that release NO spontaneously in physiological conditions are not entirely satisfactory because they release nitric oxide systemically. Nitric oxide in its pure form is a highly reactive gas having limited solubility in aqueous media (WHO Task Group on Environmental Health Criteria for Oxides of Nitrogen, *Oxides of Nitrogen,* Environmental Health Criteria 4 (World Health Organization: Geneva, 1977)). Nitric oxide, therefore, is difficult to introduce reliably into most biological systems without premature decomposition.

A number of compounds have been developed which are capable of delivering nitric oxide in biological systems. Such compounds include compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.,* 218, 739–749 (1981); Ignarro, *Annu. Rev. Pharmacol. Toxicol.,* 30, 535–560 (1990); Kruszyna et al., *Toxicol. Appl. Pharmacol.,* 91, 429–438 (1987); Wilcox et al., *Chem. Res. Toxicol.,* 3, 71–76 (1990)), which are relatively stable but release nitric oxide only on activation. While this feature may be an advantage in some applications, it also can be a significant liability. For example, tolerance to glyceryl trinitrate can develop via the exhaustion of the relevant enzyme/cofactor system (Ignarro et al., *Annu. Rev. Pharmacol. Toxicol.,* 25, 171–191 (1985); Kuhn et al., *J. Cardiovasc. Pharmacol.,* 14 (Suppl. 11), S47–54 (1989)). Also, prolonged administration of nitroprusside results in the metabolic production of cyanide, which leads to toxicity (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369). S-Nitroso-N-acetylpenicillamine has been reported to release nitric oxide in solution and to be effective at inhibiting DNA synthesis (Garg et al., *Biochem. and Biophys. Res. Comm.,* 171, 474–479 (1990)). This and other S-nitrosothiols are widely considered to release No without activation, but it has recently been shown that trace metal ions can profoundly catalyze this process (McAninly et al., *J. Chem. Soc. Chem Commun.,* 1758–59, 1993), suggesting that reports of their "spontaneous" NO generation may have depended on unnoticed catalytic effects. It has also been demonstrated that spontaneous NO release cannot account for in vitro vaso relaxation by S-nitrosothiols (Kowaluk and Fung, *J. Pharmacol., Exp. Ther.,* 255, 1256–1264, 1990.)

A class of NO donor agents that release NO truly spontaneously, i.e., without activation, is the nitric oxide-nucleophile complexes known as diazeniumdiolates, also known as NONOates, which are described in the scientific literature (e.g., Drago, *ACS Adv. Chem. Ser.,* 36, 143–149 (1962); Longhi and Drago, *Inorg. Chem.,* 2, 85 (1963). Maragos et al., *J. Med. Chem.,* 34, 3242–3247 (1991)), and in U.S. patents as referred to below. Recently, a method for treating cardiovascular disorders in a mammal with certain nitric oxide-nucleophile complexes was disclosed, e.g. in U.S. Pat. No. 4,954,526. These compounds contain the anionic $N_2O_2^-$ group or derivatives thereof. See also, Maragos et al., supra. Many of these compounds have proven especially promising pharmacologically because, unlike nitrovasodilators such as nitroprusside and nitroglycerin, they release nitric oxide without first having to be activated. The only other series of drugs currently thought to be capable of releasing nitric oxide purely spontaneously is the S-nitrosothiol series, compounds of structure R—S—NO (Stamler et al., *Proc. Natl. Acad. Sci. U.S.A.,* 89, 444–448 (1992)); however, the R—S—NO→NO reaction is kinetically complicated and difficult to control (Morley et al., *J. Cardiovasc. Pharmacol.,* 21, 670–676 (1993)). Similarly, compounds of the sydnonimine series like molsidomine and linsidomine not only require activation to release NO, but they also release undesirable free radicals. The diazeniumdiolates (NONOates), therefore, have the advantage among currently known drugs that in anionic form, they decompose at any given pH by a first-order reaction to provide doses of nitric oxide that can be predicted, quantified, and controlled. See, e.g., Maragos et al., supra.

Nitric oxide/nucleophile complexes which release nitric oxide in aqueous solution are also disclosed in U.S. Pat. Nos. 5,039,705, 5,155,137, 5,185,376, 5,208,233, 5,212,204, 5,250,550, 5,366,997, 5,389,675, 5,405,919, as well as in pending U.S. patent application Ser. No. 08/344,157 filed Nov. 23, 1994, as being useful as cardiovascular agents and for other biological indications (see also Maragos et al., *J. Med. Chem.,* 34, 3242–3247 (1991)).

Despite the promise of the diazeniumdiolates that have been investigated, their pharmacological application has been limited by their tendency to distribute evenly throughout the medium. Such even distribution is a great advantage in many research applications, but tends to compromise their selectivity of action. One of the objects of the present invention overcomes this limitation by enabling concentrated and localized release of NO at a given site in a controllable and predictable manner such that effective dosing may be realized while minimizing exposure of other NO-sensitive sites in the body.

Attempts to provide nitric oxide in vivo for the treatment of shock have involved the administration of nitric oxide-containing compounds which release nitric oxide systemically. Donor compounds which systemically release nitric oxide are not satisfactory for the treatment of sepsis and shock, however. Systemic release of nitric oxide may result in inadequate delivery of nitric oxide to the tissue injured or at risk of injury during sepsis or shock, due to the chemical destruction of nitric oxide, such as by the oxidation of nitric oxide by oxyhemoglobin in the blood before it reaches the target tissue. Systemic delivery of nitric oxide may also result in dangerous side effects, such as, for example, hypotension or the like.

In view of the disadvantages inherent in the use of nitric oxide-containing compounds that release nitric oxide systemically, it is a primary object of the present invention to provide a method of protecting an organ injured or at risk of injury during sepsis or shock which does not rely on release of nitric oxide systemically, but which releases nitric oxide with more specificity for the tissue at risk. It is a related object of the invention to provide for such delivery in a controlled and predictable manner. It is another object of the present invention to provide a method of delivering nitric oxide to tissue injured or at risk of being injured during sepsis or shock. It is a related object of the present invention to provide a method of delivering nitric oxide to tissue injured or at risk of being injured during sepsis or shock by a nitric oxide-containing compound that releases nitric oxide primarily at the tissue at risk. A further related object of the invention is to provide a method of delivering nitric oxide to tissue injured or at risk of being injured during sepsis or shock by a nitric oxide-containing compound that is concentrated and/or selectively metabolized in the liver or kidneys to release nitric oxide locally in these organs. These and other objects and advantages of the present invention, as well as additional inventive features, will be apparent from the description of the invention provided herein.

BRIEF SUMMARY OF THE INVENTION

The present invention provides a method of treating mammalian tissue which is injured or is at risk of injury during sepsis or shock, including septic shock, hemorrhagic shock and cardiogenic shock. Nitric oxide is delivered to target tissue or cells in a controlled and predictable manner through the administration of a nitric oxide-containing compound that is protected from the systemic release of nitric oxide under physiological conditions, and/or that is concentrated in at-risk organs before releasing its NO. The nitric oxide-containing compound releases a sufficient amount of nitric oxide under controlled conditions in the target tissue to protect the tissue that is injured or is at risk of injury. The nitric oxide-containing compound is desirably a diazeniumdiolate, in the form of a prodrug whose nitric oxide protective group is removed metabolically by the target tissue, e.g. the liver or kidneys, thereby assuring principal release of nitric oxide at the tissue of interest.

DESCRIPTION OF THE PREFERRED EMBODIMENTS

Figure 1:
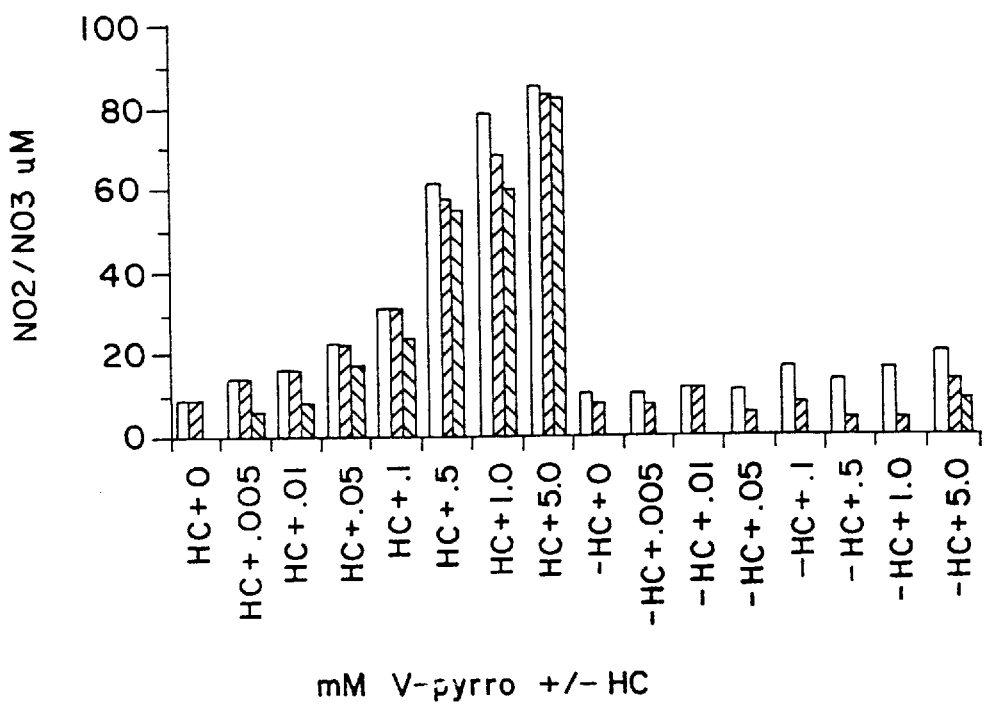
FIG. 1 is a bar graph which shows the amount of apparent nitric oxide generation as measured by the accumulation of its oxidation products, nitrite and nitrate, in cultures of hepatocytes versus controls, for varying concentrations of V-PYRRO/NO.

The present invention provides a method for using diazeniumdiolates (NONOates) that are capable of releasing NO under physiological conditions to treat mammals with sepsis or shock. The present invention provides a method of treating mammalian tissue, and human tissue in particular, injured or at risk of injury during sepsis or shock, with nitric oxide. In accordance with the method of the present invention, nitric oxide is selectively delivered to vulnerable organs or tissue, in a controlled and predictable manner, by administering a diazeniumdiolate in an amount sufficient to protect the organ or tissue at risk to damage due to sepsis or shock.

In the preferred embodiment of the present invention, the nitric oxide-containing compound is administered as a prodrug. A chemical protecting group prevents the prodrug from releasing nitric oxide until the protecting group is removed. Preferably the protecting group is removed metabolically by the tissue to be treated in order to concentrate nitric oxide at that tissue. Thus, by way of illustration, and not in limitation, where the tissue to be treated with nitric oxide is the liver, the nitric oxide-containing prodrug is inhibited from nitric oxide release with a protecting group that is metabolically removed by at least one enzyme in the liver. In this way, systemic release of nitric oxide is minimized, or even avoided completely. Importantly, nitric oxide release is largely concentrated in the liver.

In keeping with the present invention, the diazeniumdiolates (NONOates) are particularly useful. The NONOates have been shown to release nitric oxide in a predictable manner under physiological conditions (Maragos et al., *J. Med. Chem.*, 34, 3242–3247 (1991)). The half-lives of the underivatized NONOates can range from 1 minute to several days (Hrabie et al., *J. Org. Chem.*, 58, 1472–1476 (1993)) and, accordingly, offer advantages over other types of NO donor compounds, by offering a variety of spontaneous NO release rates in solution. The NONoates have been employed in various studies of cytostasis (Maragos et al., *Cancer Res.*, 53, 564–568 (1993)), cytotoxicity, mutagenicity (Wink et al., *Science*, 254, 1001–1003 (1991)), nitric oxide-mediated dopamine release in nerve cell cultures, and nitric oxide-mediated inhibition of platelet aggregation (Keefer et al., in *Biology of Nitric Oxide*, 2, *Enzymology. Biochemistry, Immunology*, Moncada et al., eds., Portland Press, Chapel Hill, N.C., pages 153–156, (1992)). Vasorelaxation of aortic rings was shown to correlate linearly with the amount of nitric oxide release from the NONOates (Maragos et al., *J. Med. Chem.*). NONOates also have been shown to be effective in the treatment of cardiovascular disorders and hypertension (U.S. Pat. Nos. 4,954,526, 5,155,137, and 5,212,204 and WO 93/07114) and have been suggested to be effective in cancer chemotherapy (Maragos et al., *Cancer Res.*, 53, 564–568 (1993)). The potential utility of the NONOates in other biomedical applications also has been suggested (Maragos et al., *J. Med. Chem.*, 34, 3242–3247 (1991); Keefer et al.(1992), supra).

Several types of NONOates are suitable for use in the method of the present invention, as described more fully below. One type useful for treating tissue injured or at risk of injury during sepsis or shock are the NONOates described in U.S. Pat. No. 4,954,526 of the formula:

[RN(H)N(NO)O]$_y$X    (Formula I)

In the compound of Formula I, R is loweralkyl, aryl, arylalkyl or cycloalkyl, and the R group may be substituted by 1–3 substituents, which may be the same or different, including halo, hydroxy, $C_1$–$C_8$ alkoxy, amino, amido, formyl, carboxy, and nitro; and X is a pharmaceutically acceptable cation, a pharmaceutically acceptable metal center, or a pharmaceutically acceptable organic group selected from the group consisting of a $C_1$–$C_8$ alkyl, acyl, and amido; and y is 1 to 3 and is consistent with the valence of X.

Where R is loweralkyl, R may be a branched or straight chain hydrocarbon radical of 1–8 carbon atoms, including, for example, methyl, ethyl, propyl, isopropyl, butyl, 2-butyl, tert-butyl, amyl, isoamyl, hexyl, heptyl, octyl, and the like. When R is an aryl, R may be an aromatic cyclic hydrocarbon radical of 6–10 carbon atoms, such as phenyl, naphthyl and the like or a heterocyclic nitrogen-containing radical such as pyrrolyl, pyrrolidinyl, pyridinyl, piperidinyl, quinolinyl, isoquinolinyl, and the like. When R is cycloalkyl, R may be a nonaromatic cyclic hydrocarbon radical of 3–10 carbons, such as cyclopropyl, cyclopentyl, cyclohexyl, cycloheptyl, cyclooctyl, and the like. The terms "halo" and "halogen" are intended to include fluorine, chlorine, bromine, and iodine. Other terms should be given those meanings normally ascribed to such terms by those of skill in the art.

The term "pharmaceutically acceptable cation" as used for X in Formula I means any cation biologically compatible in a mammal and includes alkylammonium cations, e.g., isopropyl ammonium cation and the like; alkali metals, e.g., sodium, potassium, lithium, and the like; and alkaline earth metals, e.g., calcium, barium, magnesium, and the like. The only essential characteristic of the cation chosen is that it not be biologically incompatible in a mammal.

The term "pharmaceutically acceptable metal center" as used for X in Formula I means a central metal ion, having a valence of 1 to 3, attached by coordinate links to one or more nonmetal atoms of each of the y organic groups of the above formula. The term "central metal ion" as used in Formula I includes biologically acceptable metal ions selected from alkali metals, such as sodium, potassium, lithium, and the like; alkaline earth metals, such as calcium, magnesium, barium, and the like; transition metals, including iron, copper, nickel, zinc, and the like; Group III metals including aluminum and the like; and lanthanide series metals. The only principal requirement for the central metal ion chosen is biological compatibility in a mammal.

The term "pharmaceutically acceptable organic group" as used herein refers to those biologically acceptable organic groups that covalently bond to the compound of the above formula to form ethers and other derivatives thereof. Acceptable organic groups include lower alkyls, acyl, amido, and the like.

Additional types of nitric oxide-releasing compounds useful in the method of the present invention include the nitric oxide-releasing NONOates of Formulas II, III and IV, as described in U.S. Pat. No. 5,155,137:

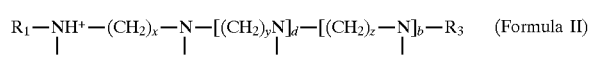

or

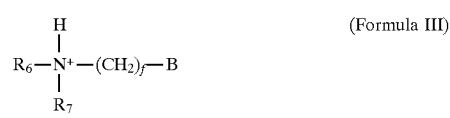

or

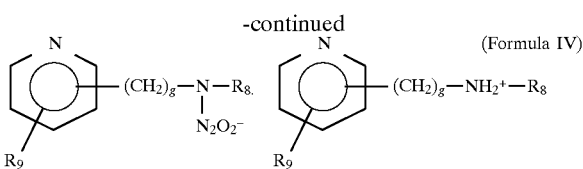

wherein b and d are independently zero or one; x, y, and z are independently 2–12; $R_1$–$R_8$ are independently hydrogen, $C_3$–$C_8$ cycloalkyl, $C_1$–$C_{12}$ straight or branched chain alkyl, benzyl, benzoyl, phthaloyl, acetyl, trifluoroacetyl, p-toluyl, t-butoxycarbonyl or 2,2,2-trichloro-t-butoxycarbonyl; $R_9$ is hydrogen or a $C_1$–$C_{12}$ straight or branched chain alkyl; B is

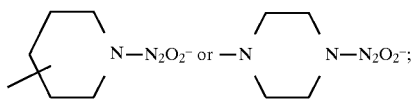

g is 2–6. The group —$N_2O_2^-$ has the structure

Preferred among the compounds of Formulas II and III are those compounds wherein $R_1$–$R_7$ are independently hydrogen, $C_{3-8}$ cycloalkyl, $C_{1-12}$ straight or branched chain alkyl, benzyl, or acetyl. More preferred are those compounds wherein $R_1$–$R_7$ are independently hydrogen, methyl, ethyl, benzyl or acetyl, and x, y and z are 2–4. Most preferred are those compounds wherein $R_1$–$R_7$ are independently hydrogen, methyl, benzyl or acetyl, and x, y and z are 2–4.

Preferred among the compounds of Formula IV are those compounds wherein $R_8$ is $C_{5-6}$ cycloalkyl, $C_{1-4}$ straight or branched chain alkyl, benzyl or acetyl. More preferred are those compounds wherein $R_8$ is methyl, ethyl, benzyl or acetyl, and most preferred are those compounds wherein $R_8$ is methyl or acetyl.

In addition to the nitric oxide-releasing compounds of Formulas I–IV, the nitric oxide-releasing compounds, as described in U.S. Pat. No. 5,212,204, are useful in the present inventive method compounds. Such compounds are defined by Formula V as follows:

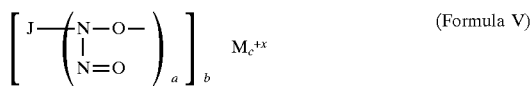

wherein J is an inorganic moiety, or an organic moiety selected from the group consisting of $C_1$–$C_{12}$ aliphatic, $C_3$–$C_8$ cycloalkyl, benzyl, phenyl, substituted benzyl, substituted phenyl, benzylcarbonyl, phenylcarbonyl, substituted benzylcarbonyl, substituted phenylcarbonyl, $C_1$–$C_{12}$ acyl, and

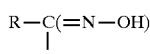

wherein R is $C_1$–$C_{12}$ aliphatic, $C_3$–$C_{12}$ aliphatic, $C_3$–$C_8$ cycloalkyl, benzyl, phenyl, substituted benzyl or substituted phenyl, and said substituted benzyl or substituted phenyl is substituted with one or two substituents selected from the group consisting of halogen, hydroxy, $C_1$–$C_4$ alkyl, $C_1$–$C_4$ alkoxy, amino, mono $C_1$–$C_4$ alkylamino, di $C_1$–$C_4$ alkylamino, phenyl and phenoxy, $M^{+x}$ is a pharmaceutically acceptable cation, where x is the valence of the cation, a is 1 or 2, and b and c are the smallest integers that result in a neutral compound.

Compounds, as described in U.S. Pat. Nos. 5,039,705 and 5,208,233, which are useful in the present inventive method, are defined by Formula VI as follows:

wherein $R_1$ and $R_2$ are independently selected from the group consisting of a straight chain or branched chain $C_1$–$C_{12}$ alkyl group and a benzyl group, or else $R_1$ and $R_2$ together with the nitrogen atom to which they are bonded form a heterocyclic group, preferably a pyrrolidino, piperidino, piperazino or morpholino group, $M^{+x}$ is a pharmaceutically acceptable cation, and x is the valence of the cation.

Compounds, as described in U.S. Pat. No. 5,389,675, which are useful in the present method, are defined by Formula VII as follows:

In the compound of Formula VII, M is a pharmaceutically acceptable metal, or, where x is at least two, a mixture of two different pharmaceutically acceptable metals, L is a ligand bound to at least one metal, and is selected from the group consisting of $C_1$–$C_{20}$ alkoxy, $C_1$–$C_{20}$ carboxylate, $C_1$–$C_{20}$ ether, $C_1$–$C_{20}$ ester, $C_1$–$C_{20}$ amide, a sulfur- or phosphorus-containing ligand, a substituted derivative of any of the above, a halide, ammonia, an aquo, a hydroxo and an oxo ligand; $R^1$ and $R^2$ may be the same of different and are selected from the group consisting of loweralkyl, aryl, and arylalky; x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary.

Compounds, as described in U.S. Pat. No. 5,366,997, which are useful in the present method, are defined by Formula VIII as follows:

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—$ON=N(O)NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom.

The compounds used in the present inventive method are preferably synthesized to include a suitable protecting group to minimize or even prevent the systemic release of nitric oxide. The protecting group must, however, be chemically or metabolically removable in the organ of interest, for selective release of nitric oxide there.

Nitric oxide protecting groups for the diazeniumdiolates described in the above Formulas may include, for example, $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; aryl or a substituted aryl, including nitroaryl, pyridyl, and the like; or groups of the formula —$(CH_2)_n$—ON=N(O)NR$_1$R$_2$, wherein n is an integer of 2–8.

The compounds used in the present inventive method are preferably soluble in physiological solutions and selectively release NO at the tissue injured or at risk of injury by sepsis or shock. By way of illustration and not in limitation, compounds that are protected from systemic release of nitric oxide and that are metabolized to NO by enzymes of the liver or kidneys are especially useful in the treatment of sepsis or shock. Use of such compounds leads to selective release of nitric oxide in the liver or in the kidneys, two organs particularly susceptible to injury from sepsis or shock. The compounds defined by the Formulas described above may be synthesized with protective groups that will minimize or even prevent systemic release of nitric oxide, and yet be metabolically removed by the enzymes of the liver and kidneys. One such compound that is especially preferred is $O^2$-vinyl 1-(pyrrolidin-1-yl)diazen-1-ium-1,2-diolate. The vinyl protecting group in this compound has been found to be metabolized by the enzyme cytochrome P540, an enzyme found in the cells of the liver and kidneys.

The compounds used in the present inventive methods may be synthesized according to methods that are well known in the art. It is preferred that appropriate amines be obtained from suitable commercial suppliers and reacted with nitric-oxide under suitable conditions to obtain the desired compound. Once a suitable amine has been synthesized or otherwise obtained (e.g., from a commercial supplier), it may then be reacted with nitric oxide to obtain a compound for use in the present invention. For example, one of the methods of. Drago et al., *J. Am. Chem. Soc.*, 83, 1819–1822 (1961), may be used to react a suitable primary amine with nitric oxide. Certain diamines may be prepared in accordance with Garrido et al., *J. Org. Chem.*, 49, 2021–2023 (1984). Certain triamines may be prepared in accordance with Bergeron, *Accts. Chem. Res.*, 19, 105–113 (1986). Bergeron, in *J. Org. Chem.*, 53, 3108–3111 (1988), also describes various methods that may be used to prepare tetraamines. Carboni et al., *Tet. Let.*, 29, 1279–1282 (1988), discloses techniques that are relevant to the preparation of di-, tri-, and tetraamines. Other methods that may be employed in synthesis are described in U.S. patents that are identified with each of the compound classes defined by Formulas I–VIII above.

The nitric oxide-releasing compounds can be used in the method of the present invention in many forms, including by way of illustration as the compounds per se or in the form of their pharmaceutically acceptable salts and derivatives. The compounds can be used alone or in appropriate combination with one or more other compounds/derivatives of nitric oxide-releasing compounds or with other active compounds. It should be understood, however, that the salt or derivative should not be one that renders the compound toxic.

The nitric-oxide releasing compounds of Formulas I–VIII can also be incorporated into a polymeric matrix as described in U.S. Pat. No. 5,405,919. Incorporation of the $N_2O_2^-$ functional group into a polymeric matrix provides a polymer-bound nitric oxide/nucleophile adduct composition that can be applied with specificity to a biological target site. Site-specific application of a polymer-bound adduct enhances the selectivity of action of the nitric oxide releasing $N_2O_2^-$ functional group. If $N_2O_2^-$ functional groups attached to the polymer are necessarily localized, then the effect of their nitric oxide release will be concentrated in the tissues with which they are in contact. If the polymer is soluble, selectivity of action can still be arranged, for example, by attachment to or derivatization of an antibody specific to the target tissue. Similarly, attachment of $N_2O_2^-$ groups to peptides that mimic the recognition sequences of ligands for important receptors provides localized concentrated effect of nitric oxide release, as would attachment to oligonucleotides capable of site-specific interactions with target sequences in a nucleic acid.

Additionally, incorporation of the $N_2O_2^-$ functional group into a polymer matrix can reduce the propensity of the nitric oxide/nucleophile adduct for the relatively rapid release of nitric oxide. This prolongs the release of nitric oxide by the $N_2O_2^-$ functional group, and allows for efficient dosing to achieve a desired biological effect so the frequency of dosing can be reduced.

The nitric oxide-releasing $N_2O_2^-$ functional groups that are bound to the polymer generally are capable of releasing nitric oxide in an aqueous environment spontaneously upon contacting the aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide releasing X[N(O)NO]$^-$ group in the vicinity of the particular cells of interest. As an example, covalent attachment of a protecting group to the anionic [N(O)NO]$^-$ function provides a means of postponing nitric oxide release until the molecule reaches an organ capable of metabolically or hydrolytically removing the protecting group. By choosing a protecting group that is selectively cleaved by enzymes specific to a cell or tissue of interest, for example, the action of the nitric oxide/nucleophile complex can be targeted to maximize the desired effect. While the polymer-bound nitric oxide releasing compositions of the present invention are capable of releasing nitric oxide in an aqueous solution, such a compound preferably releases nitric oxide under physiological conditions.

The nitric oxide releasing $N_2O_2^-$ functional group attached to a polymer is preferably a nitric oxide/nucleophile adduct, e.g., a complex of nitric oxide and a nucleophile, most preferably a nitric oxide/nucleophile complex which contains the anionic moiety X[N(O)NO]$^-$, where X is any suitable nucleophile residue. The nucleophile residue is preferably a primary (e.g., X=(CH$_3$)$_2$CHNH, as in (CH$_3$)$_2$CHNH[N(O)NO]Na) or secondary (e.g., X=(CH$_3$CH$_2$)$_2$N, as in (CH$_3$CH$_2$)$_2$N[N(O)NO]Na) amine residue or a polyamine (e.g., X=spermine, as in the zwitterion H$_2$N(CH$_2$)$_3$NH$_2$$^+$(CH$_2$)$_4$N[N(O)NO]$^-$(CH$_2$)$_3$NH$_2$, or X=3-(n-propylamino)propylamine, as in the zwitterion CH$_3$CH$_2$CH$_2$N[N(O)NO]$^-$CH$_2$CH$_2$CH$_2$NH$_3$$^+$), or a derivative thereof. Such nitric oxide/nucleophile complexes are capable of delivering nitric oxide in a biologically usable form at a predictable rate.

The nucleophile residue for polymer attachment is preferably not an entity such as that of sulfite (e.g., X=SO$_3^-$, as in $NH_4O_3S[N(O)NO]NH_4$) even though the complex is a stable compound, since it is capable of releasing nitric oxide in an aqueous environment only under harsh, nonphysiological conditions.

Other suitable nitric oxide/nucleophile complexes for attachment to a polymer include those compounds having Formulas I–VIII above.

Any of a wide variety of polymers can be used to make polymer NONOates. It is only necessary that the polymer selected is biologically acceptable. Illustrative of polymers suitable for use in the present invention are polyolefins, such as polystyrene, polypropylene, polyethylene, polytetrafluoroethylene, polyvinylidene difluoride, polyvinylchloride, other polymers such as polyethylenimine, polyethers, including polysaccharides, polyesters, polyamides such as nylon, polyurethanes, biopolymers such as peptides, proteins, oligonucleotides, antibodies and nucleic acids, starburst dendrimers, and the like.

The physical and structural characteristics of the polymers suitable for use in the present invention are not narrowly critical, but rather will depend on the end use application. For some uses, such as ingestion or the like, it may be desirable that the polymer of the polymer-bound compositions slowly dissolves in a physiological environment or that it is biodegradable.

The nitric oxide-releasing complexes having $N_2O_2^-$ functional groups, including the compounds described above, may be bound to the polymer support in a number of different ways. For example, the compounds described above may be bound to the polymer by coprecipitation of such compounds with the polymer. Coprecipitation involves, for example, solubilizing both the polymer and the nitric oxide/nucleophile compound and evaporating the solvent.

Alternatively, nitric oxide releasing $N_2O_2^-$ functional groups may be bound to the polymer by formation of a nitric oxide/nucleophile complex on the polymer itself. The $N_2O_2^-$ functional group may be attached to an atom in the backbone of the polymer, or it may be attached to a group pendant to the polymer backbone, or it may simply be entrapped in the polymer matrix. Where the $N_2O_2^-$ functional group is in the polymer backbone, the polymer includes in its backbone sites which are capable of reacting with nitric oxide to bind the nitric oxide for future release. For example, where the polymer is polyethylenimine, the polymer includes nucleophilic nitrogen atoms which react with nitric oxide to form the $N_2O_2^-$ functional group at the nitrogen in the backbone. Where the $N_2O_2^-$ functional group is attached to a group pendant to the polymer backbone, the polymer backbone contains nucleophile residues in pendant groupings that are capable of reacting with nitric oxide to form the $N_2O_2^-$ functionality. Reaction of the polymer which contains a suitable nucleophile residue, or of the suitably derivatized polymer, with nitric oxide thus provides a polymer-bound nitric oxide-releasing $N_2O_2^-$ functional group. Alternatively, preformed NONOates or derivatized NONOates can be attached via reactive groupings to the polymer.

The present inventive methods can be utilized in vitro for scientific and research purposes. However, the methods of the present invention have particular usefulness in in vivo applications, such as treating mammalian tissue injured or at risk of injury by sepsis or shock. The various types of shock that may be treated in accordance with the method of the present invention are those involving an interruption in the microcirculation in the liver and kidneys. Thus septic shock, hemorrhagic shock and cardiogenic shock may all be treated by the method of this invention. Additionally, episodes of ischemia reperfusion such as those associated with kidney transplants, liver transplants and aortic surgery where there is an interruption of blood flow to the kidneys or liver may be treated with diazeniumdiolates which selectively release nitric oxide in the liver and kidney. "Treating" means protecting against injury due to sepsis or shock, as well as protecting against the adverse consequences of shock, such as kidney or liver dysfunction. The method may be used prior to the onset of shock, or initiated as soon as sepsis or shock is diagnosed. The method is believed to accomplish the objective of treating sepsis or shock mediated tissue damage by increasing local perfusion in at risk tissue, e.g. by preventing neutrophil adherence and platelet adherence and aggregation.

Other alternatives are available for targeting the beneficial NO-releasing properties of the diazeniumdiolates to the organs at risk in sepsis or shock. For example, liposomes and microspheres are known to be sequestered rapidly in the liver following systemic administration. Liposomes containing O-protected or -unprotected diazeniumdiolate functions, prepared as taught in U.S. patent application 08/319,744, can thus be expected to localize their effect in the liver. Similarly, microspheres containing O-protected or -unprotected diazeniumdiolate groups, such as those described in U.S. patent application 08/419,424, should be selectively taken up by liver cells and thus concentrate their No-releasing properties in that organ for the patient's benefit.

To target the microvasculature of the kidney, another organ that is particularly vulnerable to shock-induced injury, alternate strategies can be employed. For example, increasing the net positive charge of a soluble polymer molecule is known to improve its filterability through the glomerular capillary wall. As a consequence, polycations containing unprotected diazeniumdiolate groups (such as those whose preparations and slow NO-release rates at physiological pH are described in U.S. Pat. No. 5,405,919 and U.S. patent application 08/344,157) can be expected to filter selectively into the Bowman' space. The fraction that releases its NO before escape into the urinary collection system will thus be free to suffuse the renal vasculature and relieve shock-induced injury to that organ. If the intrarenal pH is lower than that of the blood, NO release (which is acid catalyzed for the unprotected diazeniumdiolate) will be accelerated in the kidney, leading to even further concentration of NO's effects in that organ after systemic administration of the drug.

Yet another alternative strategy for targeting sites at risk of injury during sepsis or shock relies on attachment of O-protected or -unprotected diazeniumdiolate groups to peptides and proteins, as described in U.S. patent application 08/344,157. By this means, peptide/diazeniumdiolate conjugates can be prepared for receptor-mediated delivery of NO to vulnerable tissues. Similarly, attachment of O-protected or -unprotected diazeniumdiolate groups to appropriately tissue-specific antibodies would allow the required selective delivery of NO in sepsis or shock.

Accordingly, the present inventive methods have both prophylactic and therapeutic benefits. The present invention includes the administration to a mammal, particularly a human at risk for or having sepsis or shock tissue injury, of an amount of one or more of the nitric oxide-releasing compounds previously described or pharmaceutically acceptable salts or derivatives thereof, alone or in combination with one or more other pharmaceutically active compounds, in a pharmaceutically acceptable composition sufficient to treat the tissue that has been damaged or that is at risk to damage.

The nitric oxide-releasing compound or polymer preferably is administered as soon as possible after it has been determined that a mammal, particularly a human, is at immediate risk for sepsis or shock injury or has been diagnosed as having sepsis. It is expected that, in most situations, the nitric oxide-releasing compound will be administered when therapy has been initiated, which includes resuscitation. When it is possible to predict the onset of sepsis or shock, or ischemia followed by reperfusion, e.g. that associated with transplantation, the compound or polymer should be administered immediately upon knowledge of need. It is expected that, in transplantation situations, the nitric oxide-releasing compound will be instituted just prior to re-establishing blood flow.

One skilled in the art will appreciate that suitable methods of administering to a mammal a nitric oxide-releasing compound useful in the method of the present invention are available. Although more than one route can be used to administer a particular compound, a particular route can provide a more immediate and more effective action than another route. Accordingly, the described methods are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors including the strength (i.e., nitric oxide release capability) of the particular compound employed, the age, species, condition or disease state, and body weight of the animal, as well as the amount of cells or tissue about to be affected or actually injured or at risk of injury. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of about 0.01 to about 100 mg of one or more of the compounds or polymers described above per kg body weight over times ranging from 1 to 24 hours.

The present invention also provides a pharmaceutical composition comprising a pharmaceutically acceptable carrier and an amount of a nitric oxide-containing compound sufficient to treat shock-mediated tissue damage. The carrier may be any of those conventionally used and is limited only by chemico-physical considerations, such as solubility, and by the route of administration. It will be appreciated by one of skill in the art that, in addition to the following described pharmaceutical composition, the compounds for use in the present inventive method may be formulated as inclusion complexes, such as cyclodextrin inclusion complexes, or liposomes.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of excipient will be determined in part by the particular compound, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, intraperitoneal, rectal, and vaginal administration are merely exemplary and are in no way limiting.

Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice,* J. B. Lippincott Company, Philadelphia, Pa., Banker and Chalmers, eds., pages 238–250, (1982), and *ASHP Handbook on Injectable Drugs,* Toissel, 4th ed., pages 622–630 (1986)). It is preferred that such injectable compositions be administered intravenously.

Formulations suitable for oral administration can consist of (a) liquid solutions, such as an effective amount of the compound dissolved in diluents, such as water, saline,. or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene glycols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch.. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds or polymers of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate, and the high molecular weight adducts of ethylene oxide with a hydrophobic base. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The following examples are illustrative of, but are not in limitation of, the present invention.

EXAMPLE I

This example illustrates the synthesis of $O^2$-vinyl 1-(pyrrolidin-1-yl)diazen-1-ium-1,2-diolate (V-PYRRO/NO).

A slurry of 100 mg (0.65 mmol) of sodium 1-(pyrrolidin-1-yl)diazen-1-ium-1,2-diolate and 100 mg of anhydrous sodium carbonate in 2 ml of tetrahydrofuran was cooled to 0° C. To the mixture was added 0.5 ml of dimethylsulfoxide (DMSO) followed by 52 microliters (0.6 mmol) of 1,2-dibromoethane. The ice-bath was removed and the progress of the reaction was monitored by TLC (Silica gel, 1:1 ethyl acetate:cyclohexane). The mixture was stirred for 16 h at 25° C., diluted with 10 ml of ether and filtered through a 5 ml Fisher Brand silica gel solid extraction column. The clear eluant was concentrated on a rotary evaporator and traces of volatile components were removed under vacuum. The residue (14 mg of $O^2$-(2-bromoethyl) 1-(pyrrolidin-1-yl)diazen-1-ium-1,2-diolate) was placed in a 5 ml flask equipped with a condenser, dissolved in 2 ml of tetrahydrofuran and 250 μl of water and treated with 100 mg of powdered sodium hydroxide. The reaction mixture was heated at reflux and the progress of the elimination step was monitored on silica gel TLC (developed with dichloromethane). After 3 h the solution was allowed to cool to room temperature, diluted with 10 ml of ether and filtered through a silica gel solid extraction column. Evaporation of the solvent gave 7.8 mg (8% overall yield) of the vinyl compound, $O_2$-vinyl 1-(pyrrolidin-1-yl)diazen-1-ium-1,2-diolate.

EXAMPLE II

This Example shows that V-PYRRO/NO is metabolized only in the presence of hepatocytes.

Figure 2:
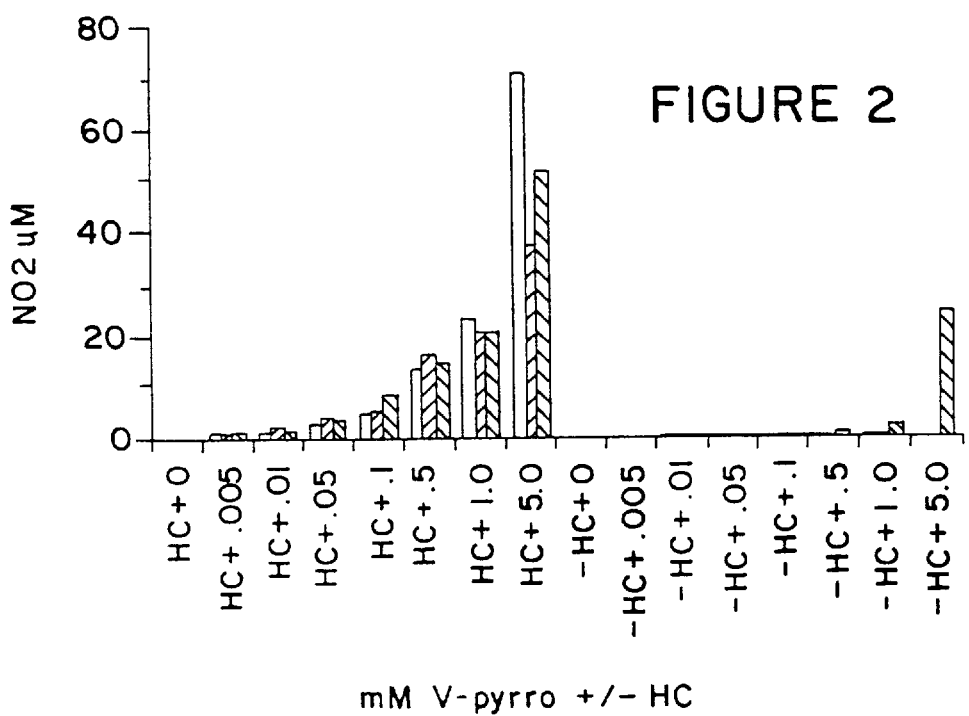
FIG. 2 is a bar graph which shows the amount of apparent nitric oxide generation, as measured by the presence of nitrite only, in cultures of hepatocytes versus controls for varying concentrations of V-PYRRO/NO.
Figure 3:
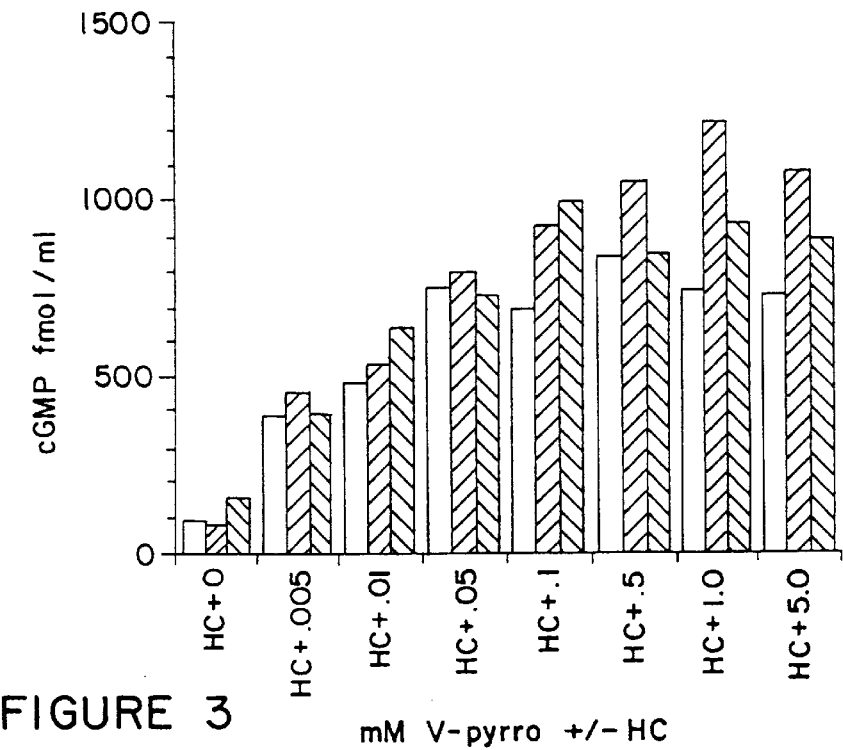
FIG. 3 is a bar graph which confirms the generation of nitric oxide, as measured by the accumulation of cGMP, in cultures of hepatocytes for varying concentrations of V-PYRRO/NO.

In this experiment, 400,000 Sprague Dawley rat hepatocytes were isolated by the collagenase perfusion technique and cultured in collagen-coated plastic tissue culture plates in 1 ml Williams Medium containing 2% cell serum with increasing concentrations of V-PYRRO/NO (range 0–5 mM). As a control, V-PYRRO/NO was incubated without cells. The concentration of $NO_2^-$, based on the Griess reaction, $NO_2^- + NO_3^-$, or cGMP in the culture supernatant was measured over a 6 h time period. FIGS. 1, 2, and 3 show the results of three identical experiments. Each bar represents the average of cultures within individual experiments.

These results show that NO is released only when hepatocytes are present, that both $NO_2^-$ and $NO_3^-$ are released as stable end products, and that biologically significant and active NO is released at the lowest concentration tested (0.005 mM) based on the release of cGMP.

EXAMPLE III

This Example illustrates that V-PYRRO/NO is metabolized by the cytochrome P450 enzymes to release NO in vitro.

Figure 4:
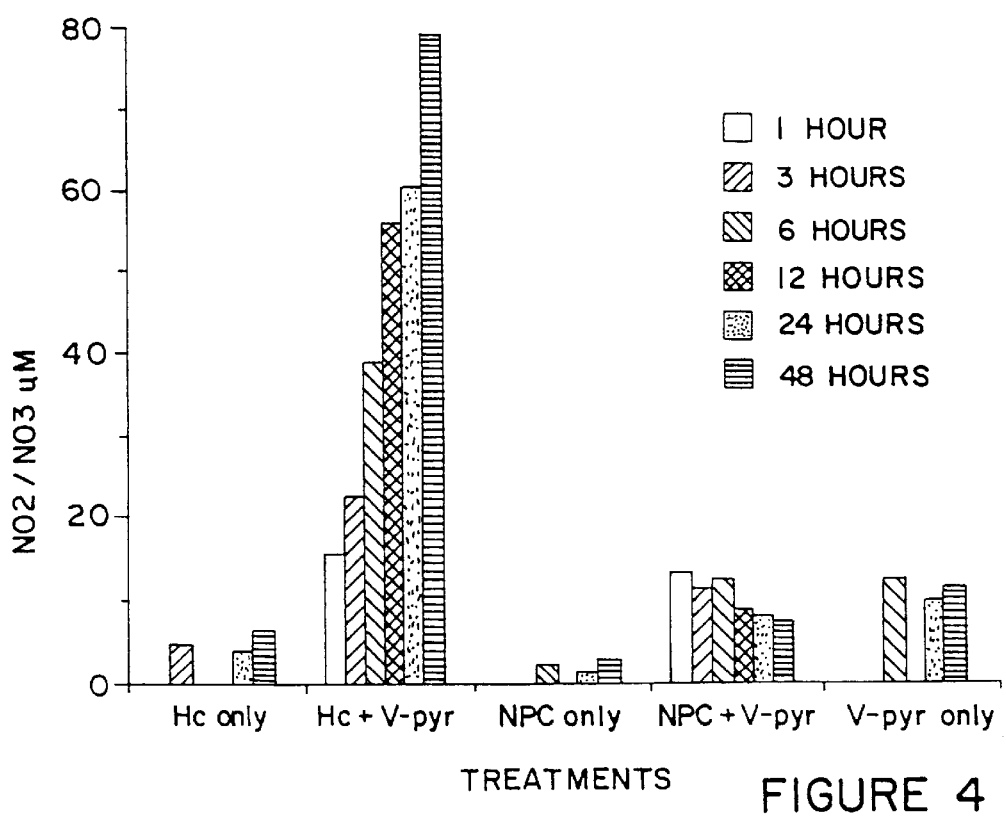
FIG. 4 is a bar graph which shows the amount of apparent nitric oxide generation as measured by the accumulation of its oxidation products, nitrite and nitrate, in cultures of hepatocytes and non-parenchymal cells in the absence of and in the presence of V-PYRRO/NO over time.
Figure 5:
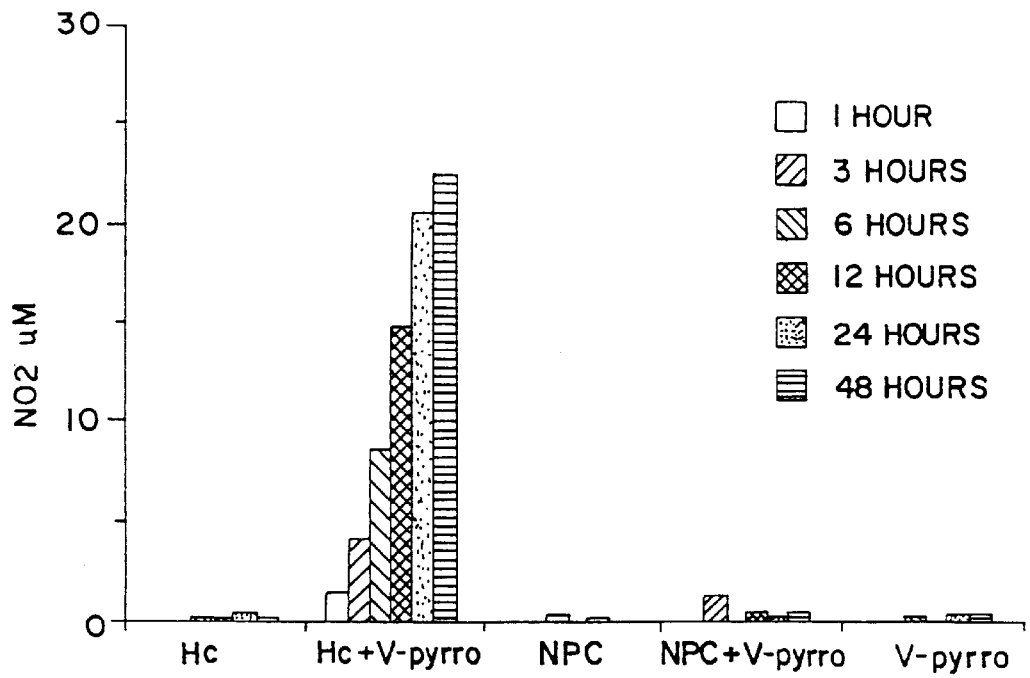
FIG. 5 is a bar graph which shows the amount of apparent nitric oxide generation as measured by the presence of nitrite only in cultures of hepatocytes and non-parenchymal cells in the absence of and in the presence of V-PYRRO/NO over time, and is confirmatory of the results depicted in FIG. 4.
Figure 6:
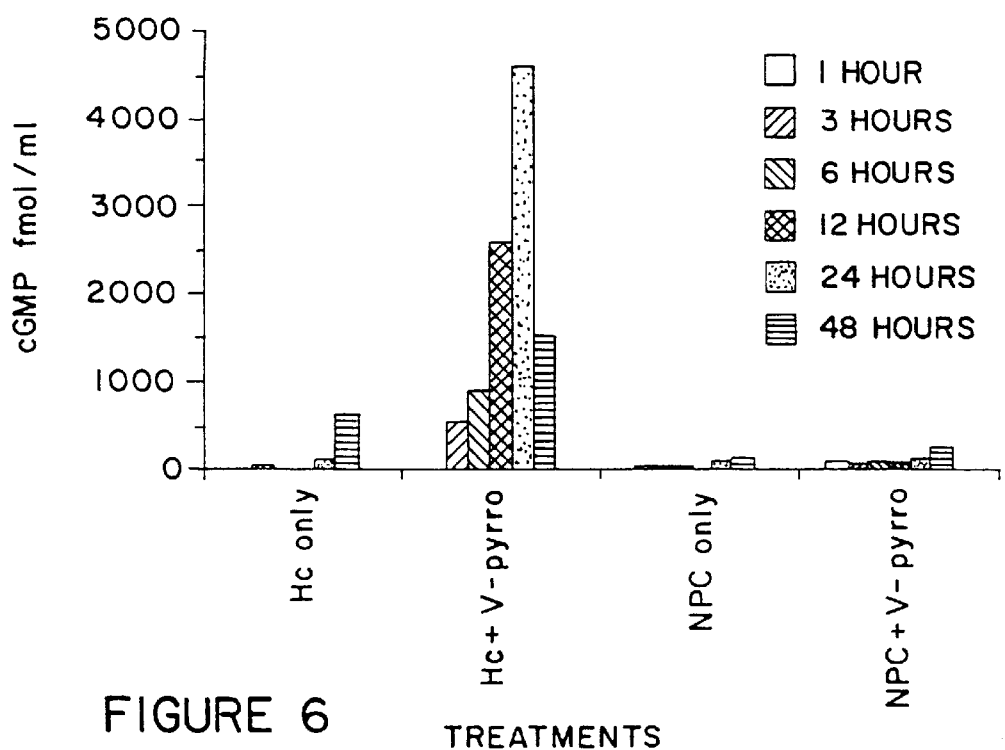
FIG. 6 is a bar graph which confirms the generation of nitric oxide, as measured by the accumulation of cGMP, in cultures of hepatocytes and non-parenchymal cells in the absence of and in the presence of V-PYRRO/NO over time.

Either 400,000 cultured rat hepatocytes (HC) or $1 \times 10^6$ nonparenchymal cells (NPC) were cultured in 1 ml of medium containing 1 mM V-PYRRO/NO and the supernatant was collected 1, 3, 6, 12, 24 or 48 hours later. Also, 1 mM v-pyrro was incubated in wells without cells as a control. The results are shown in FIGS. 4, 5 and 6. These Figures show the release of $NO_2^- + NO_3^-$, $NO_2^-$, or cGMP into the culture medium by HC and NPC.

These results show that NO release from V-PYRRO/NO is seen only with HC and not NPC, indicating a selectivity of action, namely that V-PYRRO/NO is converted to NO only in cells with cytochrome P450 enzymes.

EXAMPLE IV

This Example illustrates that V-PYRRO/NO is metabolized in vivo in a mammal with sepsis.

Figure 7:
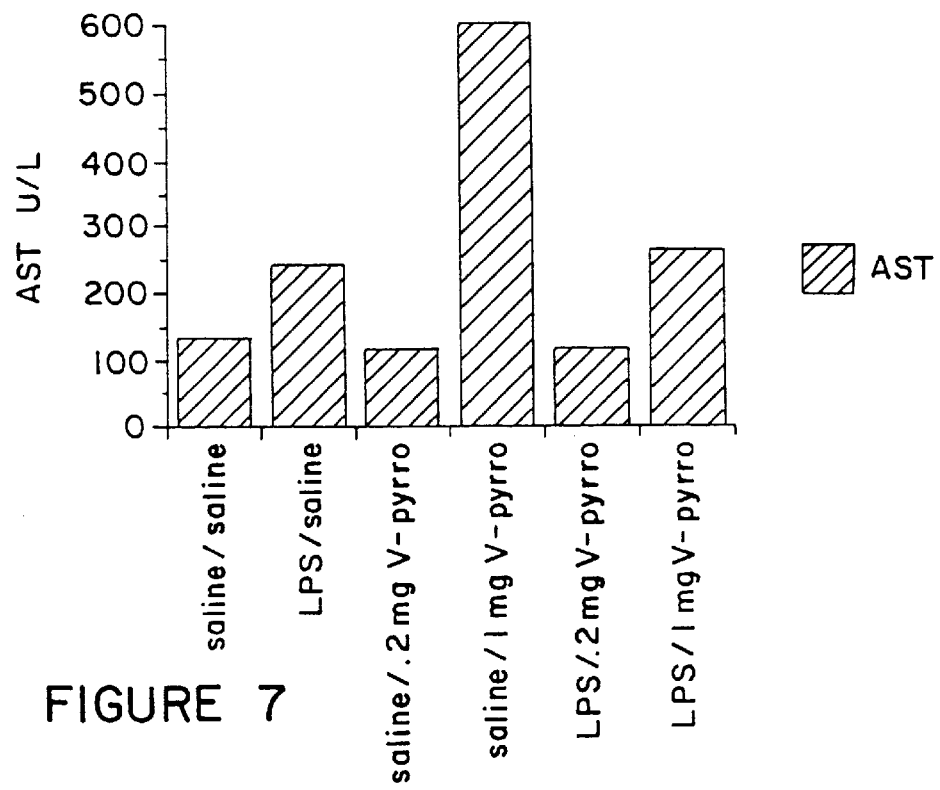
FIG. 7 is a bar graph which shows that V-PYRRO/NO induces a drop in the concentration of circulating aspartate aminotransferase (AST), a liver-injury enzyme, in mice that have been treated with bacterial endotoxin (LPS) to damage their liver.
Figure 8:
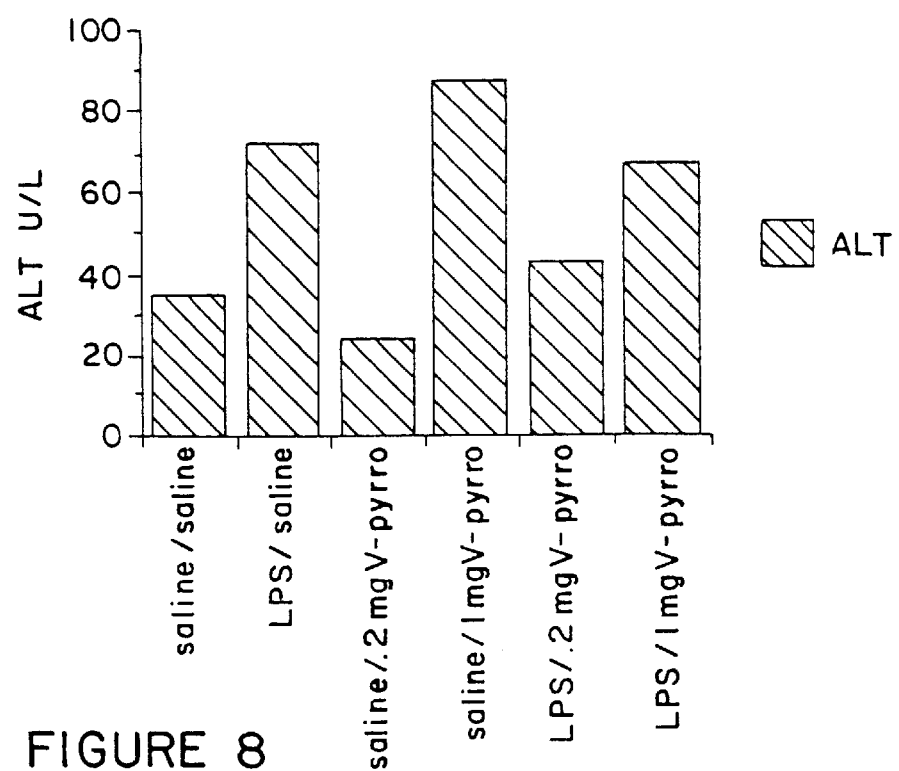
FIG. 8 is a bar graph which shows that V-PYRRO/NO induces a drop in the concentration of the enzyme alanine aminotransferase (ALT), another liver-injury enzyme, in mice that have been treated with bacterial endotoxin (LPS) to damage their livers.

Mice were injected with an intraperitoneal dose of bacterial lipopolysaccharides (LPS), 100 μgram/mouse, followed by intravenous saline (vehicle) or V-PYRRO/NO. Seven hours later the plasma was obtained and assayed for aspartate aminotransferase (AST) or alanine aminotransferase (ALT), two liver injury markers. FIGS. 7 and 8 show the results of the experiment. The 0.2 μg dose of V-PYRRO/NO was found to reduce the degree of liver injury caused by LPS injection, showing that treatment with this liver-specific NO donor protects from liver injury.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

We claim:

1. A compound of the formula:

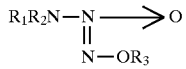

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo, or benzyl, or $R_1$ and $R_2$ together with the nitrogen atom to which they are bonded form a heterocyclic group, and $R_3$ is a vinyl group.

2. The compound of claim 1, wherein $R_1$ and $R_2$ together with the nitrogen atom to which they are bonded form a pyrrolidino, piperidino, piperazino or morpholino group.

3. The compound of claim 1, wherein said compound is $O^2$-vinyl 1-(pyrrolidino-1-yl)diazen-1-ium-1,2-diolate.

4. A composition comprising a compound of the formula:

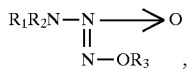

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo, or benzyl, or $R_1$ and $R_2$ together with the nitrogen atom to which they are bonded form a heterocyclic group and $R_3$ is a vinyl group.

5. The compound of claim 4, wherein $R_1$ and $R_2$ together with the nitrogen atom to which they are bonded form a pyrrolidino, piperidino, piperazino or morpholino group.

6. The composition of claim 3, wherein said compound is $O^2$-vinyl 1-(pyrrolidino-1-yl)diazen-1-ium-1,2-diolate.

7. A pharmaceutical composition comprising a compound of the formula:

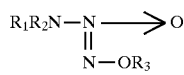

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo, or benzyl, or $R_1$ and $R_2$ together with the nitrogen atom to which they are bonded form a heterocyclic group, preferably a pyrrolidino, piperidino piperazino or morpholino group, and $R_3$ is a vinyl group and a pharmaceutically acceptable carrier.

8. The compound of claim 7, wherein $R_1$ and $R_2$ together with the nitrogen atom to which they are bonded form a pyrrolidino, piperidino, piperazino or morpholino group.

9. The pharmaceutical composition of claim 5, wherein said compound is $O^2$-vinyl 1-(pyrrolidino-1-yl)diazen-1-ium-1,2-diolate.

* * * * *